(12) United States Patent
Nikinmaa et al.

(10) Patent No.: US 12,102,841 B2
(45) Date of Patent: Oct. 1, 2024

(54) MOUTHPIECE AND METHOD FOR INTRAORAL TREATMENT

(71) Applicant: Koite Health Oy, Espoo (FI)

(72) Inventors: Sakari Nikinmaa, Aalto (FI); Jukka Kärkimaa, Aalto (FI); Tommi Pätilä, Aalto (FI); Katja Ivanitskiy, Aalto (FI); Mikko Heikkinen, Aalto (FI); Jarmo Sääski, Aalto (FI)

(73) Assignee: Koite Health Oy, Espoo (FI)

( * ) Notice: Subject to any disclaimer, the term of this patent is extended or adjusted under 35 U.S.C. 154(b) by 901 days.

(21) Appl. No.: 16/973,065

(22) PCT Filed: Jun. 10, 2019

(86) PCT No.: PCT/FI2019/050448
§ 371 (c)(1),
(2) Date: Dec. 8, 2020

(87) PCT Pub. No.: WO2019/234308
PCT Pub. Date: Dec. 12, 2019

(65) Prior Publication Data
US 2021/0244965 A1   Aug. 12, 2021

(30) Foreign Application Priority Data
Jun. 8, 2018 (FI) .................... 20185524

(51) Int. Cl.
*A61C 19/06* (2006.01)
*A61K 41/00* (2020.01)
*A61N 5/06* (2006.01)

(52) U.S. Cl.
CPC .......... *A61N 5/0624* (2013.01); *A61C 19/066* (2013.01); *A61K 41/0057* (2013.01);
(Continued)

(58) Field of Classification Search
CPC .... A61N 5/0624; A61N 5/0603; A61N 5/062; A61N 2005/0606; A61N 2005/0626;
(Continued)

(56) References Cited

U.S. PATENT DOCUMENTS 6,616,447 B1   9/2003   Rizoiu et al.
7,144,249 B2   12/2006  Rizoiu et al.
(Continued)

FOREIGN PATENT DOCUMENTS

CN   102170838 A   8/2011
CN   104379213 A   2/2015
(Continued)

*Primary Examiner* — Ankit D Tejani
*Assistant Examiner* — Joshua Brendon Solomon
(74) *Attorney, Agent, or Firm* — Laine IP Oy

(57) ABSTRACT

The invention relates to a mouthpiece and method for antibacterial treatment of intraoral surfaces. The mouthpiece comprises a body made of light-guiding material, the body comprising facial and lingual outer surfaces and facial and lingual inner surfaces adapted to face facial and lingual surfaces of teeth, respectively. A light source is attached to the body and adapted to deliver light to surfaces of teeth, the light source being positioned on at least one of said outer surfaces and adapted to deliver said light via said inner surfaces to both the facial and lingual surfaces of the teeth, wherein a portion of light is adapted to travel through said body from the facial side to the lingual side, or vice versa.

28 Claims, 3 Drawing Sheets

(52) U.S. Cl.
CPC ........... *A61N 5/0603* (2013.01); *A61N 5/062* (2013.01); *A61C 2201/00* (2013.01); *A61N 2005/0606* (2013.01); *A61N 2005/0626* (2013.01); *A61N 2005/0652* (2013.01); *A61N 2005/0659* (2013.01)

(58) Field of Classification Search
CPC .... A61N 2005/0652; A61N 2005/0659; A61N 2005/0645; A61C 19/066; A61C 19/063; A61C 2201/00; A61K 41/0057
See application file for complete search history.

(56) References Cited

U.S. PATENT DOCUMENTS

| | | | |
|---|---|---|---|
| 7,354,448 B2 | 4/2008 | Altshuler et al. | |
| 8,215,954 B2 | 7/2012 | Levine | |
| 8,241,035 B2 | 8/2012 | Jones et al. | |
| 8,371,853 B2 | 2/2013 | Levine | |
| 9,572,645 B2 | 2/2017 | Levine et al. | |
| 9,974,630 B2 | 5/2018 | Heacock et al. | |
| 2003/0097122 A1 | 5/2003 | Ganz et al. | |
| 2005/0064371 A1* | 3/2005 | Soukos | A61N 5/0601 433/29 |
| 2007/0009856 A1* | 1/2007 | Jones | A61C 17/3481 433/215 |
| 2008/0032253 A1* | 2/2008 | Montgomery | A61C 19/066 433/29 |
| 2008/0060148 A1* | 3/2008 | Pinyayev | A61B 5/0088 15/4 |
| 2009/0017422 A1* | 1/2009 | Creamer | A61C 19/066 433/215 |
| 2011/0104631 A1 | 5/2011 | Levine | |
| 2015/0164618 A1 | 6/2015 | Heacock et al. | |
| 2016/0375264 A1* | 12/2016 | Laperriere | A61N 5/0603 433/29 |
| 2017/0173353 A1* | 6/2017 | Demarest | A61C 19/066 |
| 2017/0173354 A1* | 6/2017 | Demarest | A61C 19/066 |
| 2019/0167400 A1* | 6/2019 | Barnes | A61C 17/3481 |
| 2020/0008915 A1* | 1/2020 | Vermeulen | A61C 19/066 |
| 2020/0261197 A1* | 8/2020 | Young | A61N 5/0603 |
| 2021/0038357 A1* | 2/2021 | Wang | A61N 5/062 |

FOREIGN PATENT DOCUMENTS

| | | | | |
|---|---|---|---|---|
| GB | 2475623 A | 5/2011 | | |
| KR | 20140014689 A | 2/2014 | | |
| TW | M357961 U | 6/2009 | | |
| WO | WO2018026892 A1 | 2/2018 | | |
| WO | WO-2018177795 A1 * | 10/2018 | ............ | A61C 19/06 |
| WO | WO-2019048509 A1 * | 3/2019 | ............ | A61C 19/06 |
| WO | WO-2019141834 A1 * | 7/2019 | ............ | A61C 19/066 |

* cited by examiner

MOUTHPIECE AND METHOD FOR INTRAORAL TREATMENT

FIELD OF THE INVENTION

The invention relates to oral health care. In particular, the invention relates to a mouthpiece for antibacterial treatment of intraoral surfaces, such as teeth. The invention also relates to a method of delivering light within an intraoral photodynamic treatment mouthpiece and a method of treatment of intraoral tissues.

BACKGROUND OF THE INVENTION

Oral health can be promoted by affecting bacteria inside the mouth. However, there is no effective way of managing oral bacterial load or the composition. More particularly there is no effective way to prevent or treat *Streptococcus mutans*, aka caries, bacterial infection. According to professional dentists, intraoral bacterial cleaning is required in every two months in order to keep the bacterial biofilm in check. Due to the special equipment and the particular expertise needed, this is currently impossible for most of the population.

In photodynamic treatment (PDT) oral bacteria are affected using light, in particular near-infrared (NIR) light in the wavelength range of 780-810 nm. PDT requires a lot of NIR light energy, which generates e.g. heat build-up issues and the required intensity can also be hazardous for eyes. High energy levels are needed in particular in photosensitiser-augmented intraoral PDT, such as in indocyanine green (ICG) PDT.

An intraoral treatment device is disclosed in U.S. Pat. No. 7,144,249 B2 and U.S. Pat. No. 6,616,447 B1. The device may comprise LED strip comprising LED lights covered by a transparent panel, which faces the facial surface of the teeth. There may also be provided a reflective panel behind the LED lights for maximizing the light energy targeted towards the teeth. The device is suitable for whitening the facial surface of the teeth. U.S. Pat. No. 8,371,853 B2 discloses another device suitable for the same purpose. Modifications of these device types and other existing intraoral treatment devices and methods are disclosed e.g. in U.S. Pat. No. 8,241,035 B2, U.S. Pat. No. 7,354,448 B2 and U.S. Pat. No. 9,572,645 B2.

U.S. Pat. No. 8,215,954 B2 discloses a mouthpiece comprising LEDs on the outside and inside of the dental arch so as to allow for treatment of both facial and lingual surfaces of the teeth. The device may also comprise periscopic features that deliver light evenly vertically away from the LED to a teeth surface on the respective side.

Many of the existing solutions are based on delivering light only partially to teeth surfaces with low light intensity, in which case the treatment efficiency in compromised. Further, with the present devices, there is an extensive need for LED components so as to cover all teeth surfaces. This increases the manufacturing cost of the devices and also cause a heat build-up. Typically, low-price LEDs have lower thermal efficiency, whereby a balance between cost and heat build-up is difficult to find.

Many of the proposed devices of the art also suffer from poor suitability to mass production and poor safety. For example, in some designs there are LED components placed on the biting surfaces of the teeth, whereby there is a risk of breaking the LEDs by the user biting them in accident. Also the problem of danger of NIR light to the eyes has not been solved properly.

For example because of the above-mentioned drawbacks, there are few viable consumer PDT products on the market. Efficient and safe PDT devices could, however, help make frequent antibacterial treatment available for ordinary consumers.

Thus, there is a need for improved intraoral treatment devices.

SUMMARY OF THE INVENTION

It is an aim of the invention to solve at least some of the above-mentioned shortcomings and to provide a novel mouthpiece for intraoral antibacterial treatment. Particular aims include solving, partially or totally, problems relating to efficiency of treatment and heat build-up.

Additional aims include improving user safety and manufacturability.

According to a first aspect, there is provided a mouthpiece for antibacterial treatment of intraoral surfaces. The mouthpiece comprises a body made of a light-guiding material and exhibits facial and lingual outer surfaces and at least partly light-permeable facial and lingual inner surfaces that are positioned to face facial and lingual surfaces of the teeth, respectively, when the mouthpiece is placed in position in the mouth. In addition, there is provided at least one light source attached to the body and adapted to deliver light to surfaces of teeth. According to the invention, the light source is positioned on or coupled to at least one of the surfaces of the device and adapted to deliver light via the inner surfaces to both the facial and lingual surfaces of the teeth.

The body is shaped so that a portion of light travels through the body from the facial side to the lingual side, or vice versa. Thus, a single light source, which is located away from the line of occlusion, is capable of illuminating opposite surfaces of the teeth.

According to another aspect, there is provided a method of delivering light within an intraoral photodynamic treatment mouthpiece comprising a body being made of light-guiding material and comprising facial and lingual outer surfaces, and facial and lingual inner surfaces adapted to face facial and lingual surfaces of teeth, respectively, in order to guide light thereto through the inner surfaces.

The method comprises providing light into the body through at least one of the surfaces of the body, and conducting part of the light to the facial inner surface and part of the light to the lingual surface so that at least a portion of the light travels through the body from the facial side to the lingual side, or vice versa, before exiting the body towards the teeth surfaces.

In still another aspect, there is provided an intraoral photodynamic treatment method comprising providing at least one optically active agent onto surfaces of the teeth and using the mouthpiece and method of the above kind to distribute light within the mouthpiece and to irradiate lingual and facial surfaces of the teeth.

More specifically, the invention is characterized by what is stated in the independent claims.

The invention offers significant benefits. First, by using a light-guiding material, basically only a light source is required and that light source can be placed at one side of the mouthpiece, for example on a facial or lingual outer surface. Still, each of the three surfaces of the teeth can be irradiated relatively evenly. This considerably reduces manufacturing costs and reduces heat generation during use of the device.

Second, in a preferred embodiment wherein the light source is placed on the lingual or facial outer surface of the body, heat is allowed to exit the mouthpiece efficiently towards the intraoral tissue, in particular the mucosal membrane, cheek and/or the tongue. Heat build-up within the mouthpiece is therefore reduced and the efficacy of LEDs as the preferred light source type can be kept at an optimal range.

Third, when the light source is place on an outer surface, i.e. away from the line of occlusion, improvement of user safety is reached.

Fourth, the mouthpiece can be made relatively thin at the region of occlusion, i.e. inside the dental arch, because no optic or electric components, apart from the horizontal light-guiding central body portion is needed between the upper and lower teeth. This increases user comfort.

Fifth, in preferred embodiments, the mouthpiece can be manufactured from modules that allow for lowering of manufacturing costs and individual customization for different sizes of dental archs.

Sixth, in preferred embodiments, the mouthpiece comprises a body made of light-guiding material comprising one or more H-shape elements following U-shape of dental arch, fully or partly covered with a biocompatible cover. Further, a plurality of light sources are attached to the body adapted to deliver light to surface of teeth wherein the light sources are placed between facial outer surface of the light guide and inner surface of cheek and optically coupled to H-shaped light guide elements. At least part of heat dissipation of light producing elements is conducted to oral cavity. Preferably, the maximum irradiance variation of LED coupled H-shaped element at facial and lingual inner surfaces is at maximum±90%, preferably +60%, for example±30% or less.

Seventh, as mentioned above, placement to LEDs to outer arch of teeth is preferred and will assist in keeping the LED components out from the biting range while preferably still placing the LED components in the mouth, is an advantageous feature. This embodiment allows for irradiating the tongue also, using the same light source, by letting part of the light through the lingual outer surface of the body and further to the tongue. Locating the LED components in the mouth by the side of the outer arch of the teeth is the least sensitive placement for alien objects and much to be preferred to placing the LED components on molar inner surfaces.

Eight, in preferred embodiment, the light source is positioned on or coupled to at least one of said surfaces and adapted to deliver said light via said inner surfaces to both the facial and lingual surfaces of the teeth, wherein a portion of light is adapted to travel through said body from the facial side to the lingual side, or vice versa.

The device is suitable for photodynamic non-therapeutic and therapeutic uses. It will affect the user's overall oral health by applying PDT to all of the teeth surfaces simultaneously as well as it can have special method of providing light intensity also to tongue. Heat management with high power LEDs is treatment limiting factor thus for best customer experience over 35% thermal efficacy LEDS should be used.

Placement of the LED components outside the dental arch will contribute to safety and user comfort feature. In this way, the risk of electric shock is minimized as it practically impossible to bite the LED surface.

Next, embodiments of the invention and advantages thereof are discussed in more details with reference to the attached drawings.

DETAILED DESCRIPTION OF EMBODIMENTS

Definitions

Figure 1A:
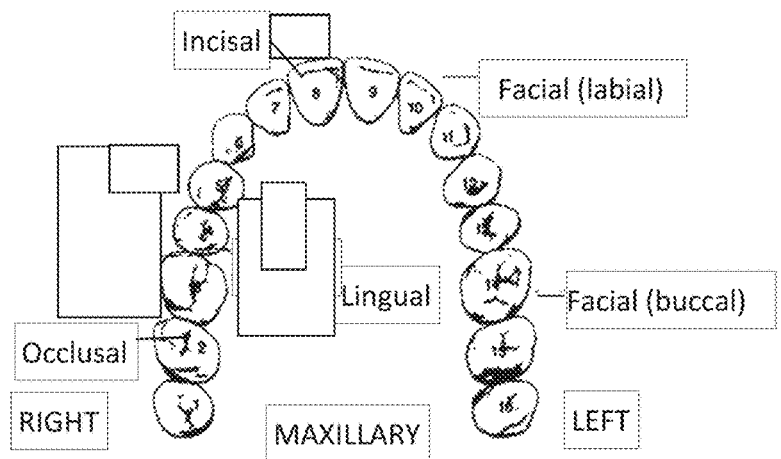
FIGS. 1A and 1B illustrate the anatomical terms relating to surfaces of the teeth and periodontal dental tissues, respectively.
Figure 1B:
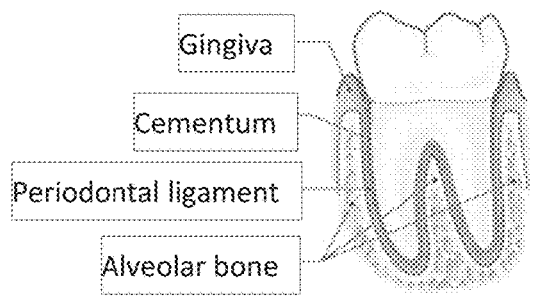

With reference also to FIG. 1A, the following anatomical terms are used to describe the geometry of the mouthpiece:

Facial surface refers to the surface of teeth that faces the cheeks or lips, i.e. outer dental arch. Used herein as an umbrella term for labial (the surface towards the lips) and buccal (the surface towards the cheeks). It is a synonym to vestibular surface.

Lingual surface refers to the surface of teeth opposite to the facial surface, i.e., the surface that faces the tongue, the inner dental arch.

Facial and lingual surfaces are both "vertical surfaces".

"Horizontal surface" refers to the incisal/occlusal surface of teeth, i.e. the biting/chewing edge/surface of anterior/posterior teeth, respectively.

The term "light diffusing" with respect to the constructional elements of the present mouthpiece is used for denoting the action of spreading out or scattering basically parallel incoming rays of light in many angles. Thus, incoming LED light will be preferably evenly spread out over the surfaces of the device facing the teeth. The term "light diffusing" also covers "light diffracting".

In the present context, the term "coupled to" when used in conjunction with the fitting of the light source to (the other parts of) the mouthpiece stands for an optical and/or mechanical joining of the light source to the mouthpiece so as to allow for the conduction or transfer of light into the structure of the mouthpiece.

The "light guiding material" is typically light transmissive and it comprises for example a transparent polymer material or article. Suitable polymers are represented by polyethylene terephthalate (PET), polycarbonate and polyacrylic materials. The materials may also include polymeric materials selected from epoxy and urethane materials as well as polyolefins, such as polyethylene and polypropylene as homo- or copolymers.

The light guiding material can be in the form of a sheet or plate which has been shaped into a mouthpiece. The wall thickness of the mouthpiece varies generally in the range of about 0.1 to about 10 mm.

The refractive index of the light guiding material can for example be equal to or greater than about 1.4. In one embodiment, the refractive index of the light guide layers is in the range from about 1.4 to about 1.7.

Generally, the present mouthpiece for antibacterial treatment of intraoral surfaces comprises a body made of light-guiding material, comprising facial and lingual outer surfaces and facial and lingual inner surfaces adapted to face facial and lingual surfaces of teeth, respectively. There is a light source attached to the body and adapted to deliver light to surfaces of teeth, which light source is coupled to or positioned on at least of the surfaces of the device, preferably on one of the outer surfaces and adapted to deliver light via the inner surfaces to both the facial and lingual surfaces of the teeth when the mouth piece is placed on the user's teeth. At least a portion of light is adapted to travel through the body from the facial side to the lingual side, or vice versa.

In some embodiments, the body comprises also a light-permeable horizontal, i.e. incisal/occlusal inner surface, facing a horizontal surface of teeth. The light source is adapted to deliver a portion of light to the horizontal surface of teeth via the horizontal inner surface. In practice, a portion of light propagating through the body, from one side of the dental arch to another, is diffused out of the body towards the horizontal surfaces, while another portion of light continues to the vertical surface farther from the light source. In some embodiments, the body comprises said facial and lingual inner surfaces, and optionally said horizontal inner surface, separately for corresponding surfaces of the upper and lower teeth. The light source can be adapted to deliver light simultaneously to at least four surfaces, preferably to all six surfaces, of the upper and lower teeth. This way simultaneous treatment of both the upper and lower teeth with a single device in a single position, is possible.

In some embodiments, the mouthpiece comprises a body made of light-guiding material comprising one or more H-shape elements which following the U-shape of the dental arch, fully or partly covered with a biocompatible cover. A plurality of light sources are attached to the body adapted to deliver light to surface of teeth wherein the light sources are placed between facial outer surface of the light guide and inner surface of cheek and optically coupled to the H-shaped light guide elements.

In some embodiments, the inner surfaces are at least partially diffusive surfaces. This means that they allow light to pass through, but are not completely clear so as to spread light more evenly at the teeth.

In some embodiments, at least one of the surfaces, such as inner surface(s), is a partially reflective surface. For example, the vertical or essentially vertical surface(s) adjacent or closest to the light source can be at least partially reflective so as to guide light towards other portions of the body more effectively and to achieve a more even light distribution on the treatment surfaces.

In one embodiment, the areas of the vertical surface(s), for example inner surface(s), close to the light source(s) are partially reflective so as to guide light towards other portions of the body of the mouthpiece to contribute to the spreading of light to the treatment surfaces.

In some embodiments, at least part of the outer surfaces of the body are entirely reflective for light coming from the inside of the body. Thus, they keep the light field inside the body, until light rays escape via the inner surfaces thereof facing the teeth.

In some embodiments, the body is provided with a reflective portion having a slanted profile placed on the opposite side of the body than the light source. The slanted portion serves to direct light passing the central portion of the body transversely towards the inner surfaces of the teeth on the opposite side of the dental arch than the light source. In some embodiments, the body has a general shape corresponding to the dental arch.

This allows for treatment of all teeth simultaneously. Typically, the light source for such an arrangement comprises one or more LED light sources, for example a LED array or a LED strip arranged to follow at least one of the outer surfaces of the body, i.e. on the facial and/or lingual side of the dental arch, away from the line of occlusion.

In some embodiments, the body is made of a plurality of light guide modules, which are positioned one after another in the form of the dental arch, or part thereof. As will be discussed in more detail with respect to the embodiments of the drawings, the modules are preferably linked together on adjacent surfaces such as to form a continuous light guide continuing over the joint between the individual modules. In particular, the modules can be joined together by joints, for example shaped with female and corresponding male parts which allow for assembly of the modules in a snap-on fashion. By assembling the mouthpieces from modules it is possible to build up mouth pieces which fit individual jaws. Further, in a preferred embodiment, the joints between modules in the area between the occlusal and incisal tooth surfaces are designed such as to allow for some lateral flexibility to accommodate for individual differences in the jaw.

Of the modules at least some, preferable all are typically provided with at least one light source, in particular one or more LED lights.

In some embodiments, the body has a U- or H-shaped cross-sectional profile. When a teeth or opposite tooth is placed in the recess or recesses of the U- or H-profile, the body covers and illuminates the horizontal and the two vertical surfaces of the tooth or teeth, respectively.

In some embodiments, the light source is adapted to deliver light to the tongue through the lingual outer surface of the body. This allows for treatment of tongue bacterial films simultaneously to treatment of the teeth and periodontal tissues.

In some embodiments, the light source, in particular the LED light source, is positioned on or coupled to at least one of said surfaces and adapted to deliver light via the inner surfaces to both the facial and lingual surfaces of the teeth. A portion or at least a portion of the light is adapted to travel through said body from the facial side to the lingual side, or vice versa.

In some embodiments, the body and the light source are at least partly encapsulated by a casing having a shape of the dental arch. The casing typically mechanically protects at least the light source and electrical components of the device, while allowing the treatment light to escape to desired tissues.

In some embodiments, the light source is adapted to emit light at least one non-visible wavelength band, such as at a band equaling to, covering or selected from the band of 780-815 nm.

In some embodiments, at least part of heat dissipation of light producing elements is conducted to the oral cavity. Preferably, the maximum irradiance variation of LED coupled H-shaped element at facial and lingual inner surfaces is at maximum±90%, preferably ±60% or less, for example±30% or less.

In some embodiments, the device comprises at least one sensor, such as an optical sensor, for measuring the response of intraoral tissue or intraoral agent to light emitted thereto, such as photo-bleaching of active ingredient or amount of active ingredient in the treatment area. There may be also other sensors, such as temperature sensors included, as will be described in more detail later.

In some embodiments, there is provided a sensor and means for regulating the output power of the light source on at least one wavelength, in particular at least one non-visible wavelength band, based on output of the sensor. For example, the means for regulating the output power of the light source can be adapted to increase power output of the light source in response to detecting a particular wavelength by the sensor.

In some embodiments, the device is configured to emit visible light simultaneously to the treatment light, which is typically at the NIR region. For example, there may be provided, in addition to the treatment light source, as separate visible-light source which is configured to operate simultaneously to said light source. The visible light serves as a safety feature, as the user is able to see when the device is operative. In some embodiments, the intensity of the visible light is high enough to generate the natural and active aversion response of the eye. This results in reflexes of contraction of iris and turning head away from the light source, this protecting the eyes.

In some embodiments, the device comprises a vibrator for mechanically vibrating the body while positioned intraorally.

The present technology also provides a method of delivering light within an intraoral photodynamic treatment mouthpiece which comprises a body being made of light-guiding material and comprising facial and lingual outer surfaces. The facial and lingual inner surfaces are adapted to face facial and lingual surfaces of teeth, respectively, in order to target light thereto through said inner surfaces Further, the present technology also provides an intraoral photodynamic treatment method comprising providing at least one optically active agent onto surfaces of the teeth, positioning a mouthpiece as described herein into the mouth so that said facial and lingual inner surfaces face facial and lingual surfaces of the teeth, respectively, and delivering light within the mouthpiece and onto the facial and lingual surfaces of the teeth as disclosed above.

In an embodiment, the mouthpiece comprises a light guiding material which consists or or consists essentially of or comprises a transparent polymer material, in particular a polymer material selected from the group of polyethylene terephthalate (PET), polycarbonate and acrylic polymers.

In one embodiment, the mouthpiece comprises a light guiding material having a refractive index equal to or greater than about 1.4, in particular the refractive index of the light guiding material is from about 1.4 to about 1.7.

Turning next to the drawings, some embodiments suitable for affecting bacterial biofilm and bacterial composition of oral areas in accordance with the invention are described.

The description focuses mainly on the implementation of a full-sized mouthpiece for simultaneous treatment of all of the upper and lower teeth, but also smaller mouthpieces focusing on a portion of the dental arch and/or only upper or lower teeth can be implemented using the described principles.

Figures 2A, 2B:
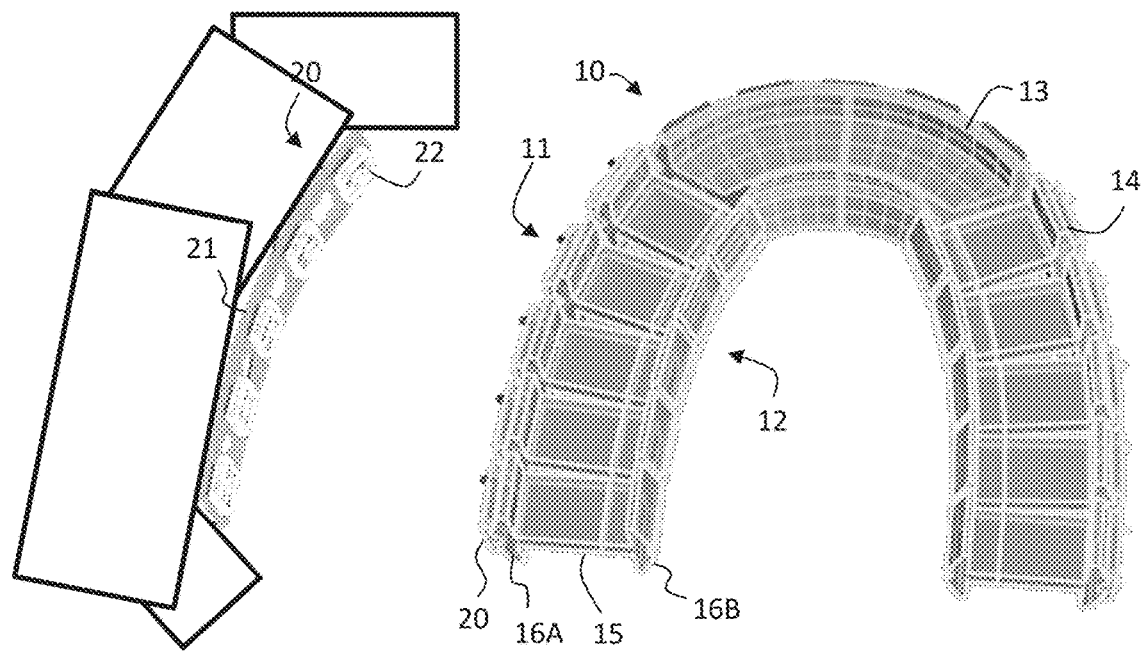
FIG. 2A shows a perspective view of a LED light strip usable in a mouthpiece according to the invention.
FIG. 2B shows a perspective top view of a mouthpiece according to one embodiment.

FIGS. 2A and 2B illustrate a body 10 of a mouthpiece and a LED light strip 20 usable therein as the light source. The body 10 has a facial outer surface 11 onto which the light strip 20 is in this example mounted, and a lingual outer surface 12.

The light strip 20 comprises a support 21 and a plurality of LED units 22 arranged therein in a row. The support 21 may be a flexible circuit board containing electrical contacts for the LED units 22 and electrical interconnections between the LED units 22 for powering them using a single power input point.

The body is in the illustrated example made of several body modules 13, 14. For the incisors, there is provided an arch-shaped front module 13 and for the molars a plurality of unit modules 14 arranged one after another and continuing from the front module 13 in the shape of the dental arch.

Each of the modules 13, 14 comprises two end portions 16A, 16B and a connecting portion arranged between the end portions 16A, 16B and optically connected therewith. The connecting portion 15 extends essentially perpendicularly to the end portions 16A, 16B. The end portions 16A, 16B are shaped so that their inner surfaces facing each other cover at least a portion of vertical surfaces of the teeth, respectively, when the mouthpiece is placed into the mouth. The connecting portion thereby 15 covers the horizontal surfaces. Each of the body modules 13, 14 can be made of a single piece of light-guiding polymer. In a two-sided configuration suitable for the treatment of both the upper and lower teeth simultaneously, as herein illustrated, the modules have an H-shaped cross-sectional profile. In a single-sided version, a U-shaped profile can be used, whereby the end portions 16A, 16B would essentially extend only to one direction from the connecting portion 15. The body modules 13, 14 can be joined to each other using any suitable connection method, such as gluing, molding, shape-based locking and/or using an additional skeleton or casing to which the body modules 13, 14 are mounted.

It should be noted that the modular construction of the body is given as a preferred embodiment only. The body can also be made of a single piece of light-guiding material, having the general shape and optical properties herein described.

It is also possible that the body of the mouthpiece consists of one, two or more body modules of the discussed kind, without taking the form of the dental arch. Such body and mouthpiece comprising such body can be used for local treatment of the teeth.

Figure 3:
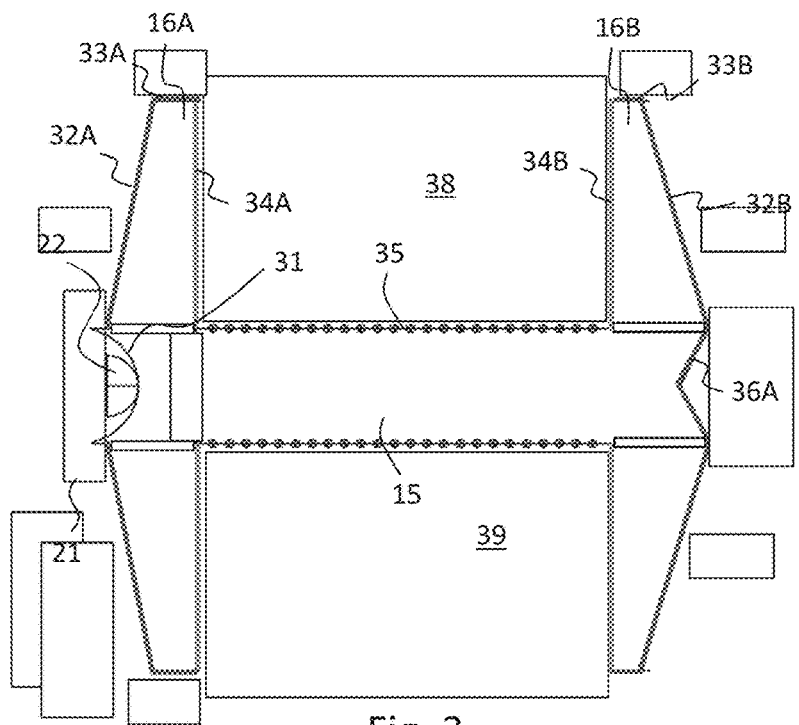
FIG. 3 shows a cross-sectional view of the mouthpiece according to one embodiment.

FIG. 3 shows in more detail an exemplary structure of the body in cross-sectional view. The end portions 16A, 16B comprise inner surfaces 34A, 34B facing each other, and outer surfaces 32A, 32B, respectively, facing outside and inside the dental arch. The outer surfaces 32A, 32B (and 33A, 33B, 36A, 36B) are preferably entirely reflective so as to prevent leakage of light from the body away from the teeth.

The inner surfaces 34A, 34B are at least partly transparent so as to allow light to exit the body towards the teeth. The inner surfaces 34A, 34B are preferably at least partly diffuse to distribute light evenly on the surfaces of the teeth.

As shown herein, the outer surfaces 32A, 32B can be arranged at an oblique (non-zero) angle with respect to the inner surfaces, such as at an angle of 3-20 degrees. The angle is provided for increasing evenness of light distribution on the inner surfaces 34A. 34B.

The central portion 15 extends substantially symmetrically between midpoints of the end portions 16A, 16B. Also non-symmetrical configuration can be envisaged. The central portion has a thickness allowing efficient guiding of light between the end portions 16A, 16B and still convenient occlusion.

The light source 20 is positioned at one side of the body, herein facing the first end portion 16A, aligned with the central portion 15. There may be provided a recess 31 in the end portion 16A so as to safely accommodate the LED unit 22 of the light source. The recess may, in some embodiments, be shaped as a concave lens surface promoting even light distribution inside the body.

When the light source is activated, light rays enter the body directly to the regions of the first end portion 16A closer to the light source and the central portion 15, and to the second end portion 16B through the central portion 15. The second end portion 16B is provided with a doubly slanted reflective surface 36A so as to spread light coming from the central portion 15 into the two branches of the end portion 16B.

To achieve maximally even distribution of light between the end portions 16A, 16B, their inner surfaces may have different optical properties. In some embodiments, the inner surface 34A of the first end portion 16A closer to the light source has a higher reflectance than that of the inner surface of the second end portion 16B, which may have essentially zero reflectance. Thereby, a significant portion of light that enters the branches of the first end portion 16A is reflected between surfaces 34A, 32B thereof and eventually guided from the first end portion 16A to the central portion 15 and further to the second end portion 16B. The optically transparent and optionally diffusive inner surface 34B of the second portion 16B lets all or at least a higher percentage of light through.

The surface 35 of the central portion 15 may be partly transparent and optionally diffusive, and partly reflective.

The desired optical behavior of the surfaces of the body can be achieved in many ways. Examples include utilization of reflective and/or diffusive coatings and/or utilization of total internal reflections at the surfaces, as determined by the index of refraction of the light-guiding body material and any optional coating thereon. Coatings can be provided on the outer surface of the body or as intermediate layers between the polymer bulk body and an optional outer shell layer thereon. Optical properties, in particular diffusivity, can be also adjusted by microstructuring the surfaces. A reflective coating may be a metal-containing coating.

The U-shaped front module 14 and unit modules 13 can operate optically in the same way. Their cross-sectional profiles may be the same or separately shaped to comfortably accommodate the incisors and molars, respectively.

The molar unit modules 14 can be straight or slightly curved in accordance with the dental arch on the molar area. Depending on their initial shape and the desired mouthpiece shape, they may be attached together so that their opposing end surfaces are at an angle with respect to each other or directly abutting each other.

In some embodiments, the front module 13 is also made of several unit modules of the same or different kind than the molar unit modules 14. In some embodiments, the front module 13 is manufactured by first making a straight elongated module e.g. by direct injection molding or joining several unit modules together and then curving the module, or by first manufacturing several curved modules and joining them together. The front module may be for example a combination of 3 to 7, such as 5, different modular pieces curved and molded together to correspond to the curvature of mouth.

In some embodiments, the front module 13 is bendable at at least one location, such as in the middle, i.e., with respect to the axis of symmetry of the dental arch, in order to allow adjust its shape. This allows for a single front module to be used with dental archs having different frontal curvatures.

The modules 13, 14 can be joined such that light is conducted also between the elements. This allows for an increase of the evenness of light distribution on the treatment surfaces. The light conducting modules described above can be used to efficiently spread the light from LED components to around the teeth. Different geometries that serve for the same purpose of distributing light from a single point of injection to several surfaces can be realized too.

The proposed light conducting modules are easy to manufacture by inject molding, for example. They can be manufactured in different sizes and/or shapes and even in one size connected to form mouthpieces of different sizes and/or shapes. Thus, the proposed configuration makes the mouthpiece and its assembly process both adaptable and scalable.

Figure 4A:
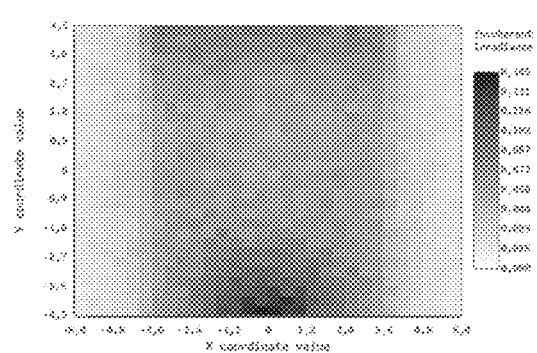
FIGS. 4A, 4B and 4C show graphs of light intensity distribution at the LED-side vertical inner surface, the horizontal inner surface and the opposite-to-the-LED-side vertical inner surface, respectively.
Figure 4C:
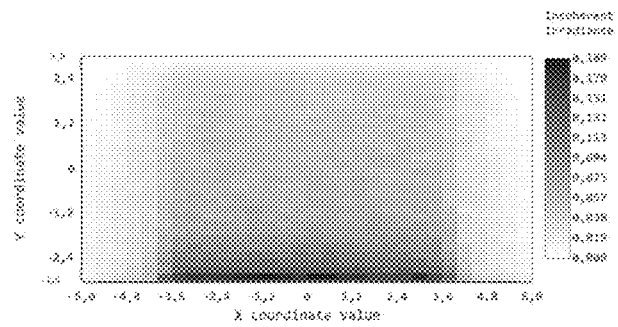
Figure 4B:
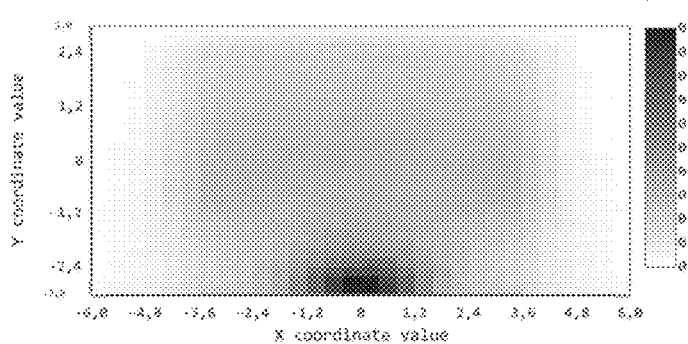

FIGS. 4A, 4B and 4C shows a simulated light intensity profiles at the inner surfaces 34A, 35 and 34B of the first end portion 16A, the central portion 15 and the second end portion 34B of a single unit module 14, respectively. It can be seen the relatively high evenness of light exposure can be achieved at each of the surfaces separately, and also between the surfaces. The evenness on the teeth surfaces can be even higher due to the diffusivity of the surfaces. The even spread of intensity ensures good treatment effect in all teeth surfaces and periodontal tissues.

From FIGS. 4A-C it can be seen that at the high intensity area closest to the led output the maximum intensity is above 300 mW/cm$^2$ but that the average intensity at the inner surface areas of the modules (light rectangular areas in the middle of the graphs) is close to 100 mW/cm$^2$.

The light source and the optical body can be configured to emit an average power density of for example 30 to 1000 mW/cm$^2$ towards the teeth. In preferred embodiments, even delivery of light at an average intensity of 50 mW/cm$^2$ or higher distributed across each of the opposing vertical and the connecting horizontal inner surfaces of the body, is achieved. In particular, the intensity emitted from the inner surfaces can be 50 mW/cm$^2$ or more at each point of the inner surfaces.

Figure 5:
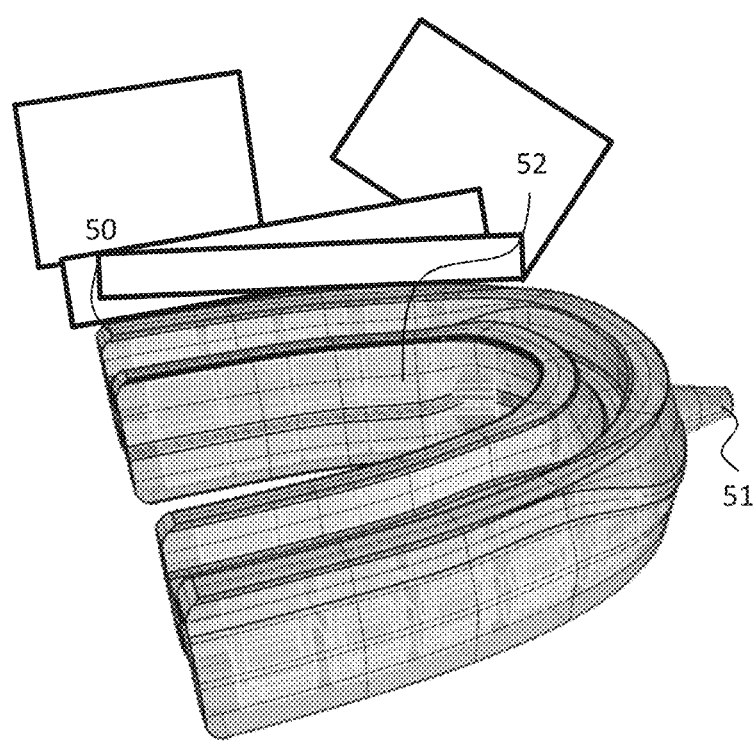
FIG. 5 shows another perspective view of the mouthpiece according to one embodiment.

Referring now to FIG. 5, in some embodiments, the light-guiding body 52, in particular a modular body of the kind discussed above, and the light source(s) together with any necessary driving electronics, are placed inside a polymeric casing 50. Power, control signal, and/or any active ingredients required by the treatment, may be delivered to the mouthpiece through on or more electric or fluid inlets 51. The casing may be at least partially transparent or open so as to allow for treatment light to exit to the desired intraoral surfaces.

The casing, like the optical modules therein too, can be manufactured by injection molding or 3D printing, to mention some examples.

In some embodiments, the treatment effect is generated with photo dynamic or photo catalytic effect that happens when light is absorbed to active ingredient or compound. The treatment effect can be enhanced with antioxidant molecules such as vitamin E or with pigments to selectively shield "good" bacteria flora. Treatment can be done with single active ingredient with single effective wavelength or multiple ingredients can be used together with specific spectrum of light.

One potential combination of ingredients is indocyanine green (810 nm) and titanium dioxide (405 nm). This combination can be further enhanced by adding antioxidants (E-vitamin or its analogue) and/or pigment.

Active ingredients can be spread to mouth in form of paste that can be either brushed to teeth or added to the mouth piece surface. Active ingredients can also be in a form of mouth rinse. Alternatively, the ingredients may be provided through one or more channels provided in the mouthpiece, in particular the casing thereof.

Photo dynamic treatment (PDT) typically requires large amounts of light energy per area (usually on the order of 20-100 J/cm$^2$), for example 100 mW/cm$^2$ at a minimum. This, combined with short usage time window, results in requirement of high intensity radiation that can be dangerous for the device user, in particular due to the risk of retinal burn. The problem is of particular significance in applications where NIR light with having intrinsically visual stimulus or blue light with high retinal blue hazard are used. This problem can be mitigated using two ways. First, by utilizing light diffusing elements, for example as described above, the intensity distribution is spread evenly on the internal surfaces of the device, even with high power LED components. Second, it may be arranged so that some amount of visible light is always provided together with the treatment light, such as NIR light. The visible light escapes the mouthpiece through the same surfaces as the NIR light. This forms a built-in safety feature, which also serves to inform the user when the device is powered and ready to use. The visible light may originate from the same or different LED component than the actual treatment radiation.

The mouthpiece may comprise a built-in electric power reservoir, such as a battery or supercapacitor for powering the light source(s) and any other electronic functions that the mouthpiece incorporates. In some embodiments, the power reservoir can be charged wirelessly.

Power can be switched on for example automatically when disconnected from the charger or manually when the user bites the mouthpiece, as detected by a suitable sensor. In one embodiment, the power storage is implemented using one or more supercapacitors which can drive the device at least for 15 minutes, such as 15-30 minutes. There may for example be one supercapacitor per one or a group of LEDs. Supercapacitors capable of powering one LED ta least for 15 minutes, such as 15-30 minutes, are available.

The device can also have one or more sensors. This allows for providing a measurement and/or feedback functionality to the treatment process. In some embodiments, at least one sensor is provided for measurement of light absorption of LED components from LED current. In alternative or supplementary embodiments, there may be provided at least one photosensitive element, such as a diode, capable of measuring light absorption. Light absorption information can be linked to amount of biofilm on top of teeth and to early onset of caries.

In some embodiments, the mouthpiece is provided with a sensor for measure change in absorbed light of the emitted wavelength or wherein the component associated with the sensor output emits light of a first wavelength, and the sensor input detects light of a second wavelength different than the first wavelength.

In some embodiments, the mouthpiece is provided with one or more temperature sensors adapted so measure the temperature of the light sources or their surroundings. There may also be means for continuous monitoring of the temperature and for limiting LED power if the temperature rises to a predefined level. This will keep the user safe and allow LEDs to stay in their optimal zone for best thermal efficacy.

In some embodiments, the mouthpiece surface is at least partially coated with small layer of titanium dioxide that will produce reactive oxygen as 405 nm light is emitted from the structure. Titanium dioxide can be used as a diffracting material in the mouthpiece and it also has a therapeutic bacteria-killing function as such.

In some embodiments, the It is also possible to make light weight PDT device for low effect local use by using only one or two modular elements with limited electronic components. Charging of mouthpiece is done wirelessly to super capacitor. The device lights up when lifted from charger.

In some embodiments, the mouthpiece is provided with a self-antibacterial function by having an antibacterial layer thereon and irradiating the antibacterial layer, for example periodically when in standby-mode, e.g. in a charger. For example, the mouthpiece may provide 405 nm light to titanium dioxide particles contained in the mouthpiece In one exemplary use case, the treatment is started by applying the active ingredient product to mouth and then placing the mouthpiece into the mouth and connecting the mouthpiece with an external control unit by a cord or wirelessly. The control unit can be a mobile device which is easy to carry during the treatment. After completed treatment, the may take a probiotic product in form of gum, tablet, paste or liquid, for example.

To further concretize and summarize the described embodiments, the present mouthpiece is capable of distributing light relatively evenly to dental and periodontal locations, when a LED light source is located at the facial or lingual surface of the teeth. Facial or lingual surface location of the LEDs, i.e. the area between the lips or cheeks and the tooth, or the location between the teeth and the tongue enables thermal loss into the surrounding tissues during the light exposure. Furthermore, the LED location away from the occlusal surfaces of the teeth reduce the risk of breaking the LED part by biting. Optical attributes of the modular elements in the mouthpiece enable an even light distribution on all surfaces of the teeth. The LED elements may have over 35% thermal efficacy.

Thus, it is preferred to place the LEDs to the outer arch of teeth since this will assist in keeping the LED components out from the biting range while preferably still placing the LED components in the mouth. This embodiment allows for irradiating the tongue also, using the same light source, by letting part of the light through the lingual outer surface of the body and further to the tongue. Locating the LED components in the mouth by the side of the outer arch of the teeth is the least sensitive placement for alien objects and much to be preferred to placing the LED components on molar inner surfaces.

In some embodiments, the present photodynamic therapy mouthpiece has one or more safety features that prevent user to harm himself with high intensity invisible light. In one implementation, a safety feature is based on regulating the brightness of the light source(s) for light components outside of 390-700 nm wavelengths based on a sensor input of the device or include additional light source of emitting light in the visible 390-700 nm spectrum to generate the natural and active aversion response of the eye to bright light. The device may additionally be configured to turn from low power to high power state once detecting target wavelength from treatment area that is inherent to a target molecule. Some embodiments utilize 780-815 nm light as primary active light and bright white light as eye-protecting light.

In some embodiments, the device is configured to switch from low power to high power treatment radiation only after detecting fluorescence radiation from its target area by as sensor, and thus protecting eyes and other tissues from unnecessary exposure to radiation.

Abbreviations

LED light-emitting diode
PDT photodynamic treatment
NIR near-infrared (light)
ICG indocyanine Citations List

PATENT LITERATURE

U.S. Pat. No. 7,144,249 B2
U.S. Pat. No. 6,616,447 B1
U.S. Pat. No. 8,371,853 B2

U.S. Pat. No. 8,241,035 B2
U.S. Pat. No. 7,354,448 B2
U.S. Pat. No. 9,572,645 B2
U.S. Pat. No. 8,215,954 B2

The invention claimed is:

1. A mouthpiece for antibacterial treatment of intraoral surfaces, the mouthpiece comprising:
   a body made of light-guiding material, the body comprising:
      facial and lingual outer surfaces, and
      facial and lingual inner surfaces adapted to face facial and lingual surfaces of teeth, respectively, and
   a light source attached to the body and adapted to deliver light to surfaces of teeth, wherein
   the light source is positioned on or coupled to at least one of said surfaces and adapted to deliver said light via said inner surfaces to both the facial and lingual surfaces of the teeth, wherein a portion of light is adapted to travel through said body from the facial side to the lingual side, or vice versa, and
   wherein the body comprises a reflective portion having a slanted profile and placed on the opposite side of the body than the light source for directing light towards the inner surfaces of the teeth on the opposite side of the teeth than the light source.

2. The mouthpiece according to claim 1, wherein:
   the body comprises also a horizontal inner surface, facing an incisal and/or occlusal horizontal surface of teeth, and
   the light source is adapted to deliver a portion of said light to said horizontal surface of teeth via said horizontal inner surface.

3. The mouthpiece according to claim 2, wherein the body comprises said facial and lingual inner surfaces, and optionally said horizontal inner surface, separately for corresponding surfaces of the upper and lower teeth, and said light source is adapted to deliver light simultaneously to at least four surfaces, preferably to all six surfaces, of the upper and lower teeth.

4. The mouthpiece according to claim 1, wherein at least one of said inner surfaces is an at least partially diffusive surface and at least one of said outer surfaces is a partially reflective surface.

5. The mouthpiece according to claim 1, wherein the surface(s) closest to the light source are partially reflective so as to guide light towards other portions of the body of the mouthpiece and to achieve light distribution on the treatment surfaces.

6. The mouthpiece according to claim 1, wherein inner facial or lingual inner surface of the body closer to said light source is a partially reflective surface so as to spread light evenly between the facial and lingual inner surfaces of the teeth.

7. The mouthpiece according to claim 1, wherein at least part of the outer surfaces of the body are reflective, as seen from the inside of the body.

8. The mouthpiece according to claim 1, wherein the body has a shape corresponding to the dental arch.

9. The mouthpiece according to claim 1, wherein the body is made of a plurality of light guide modules, which are positioned one after another in the form of the dental arch.

10. The mouthpiece according to claim 1, wherein the light source comprises one or more LED light sources positioned at and arranged to follow the shape of the facial and/or lingual outer surface of the body.

11. The mouthpiece according to claim 1, wherein the light source is positioned on the facial outer surface of the body.

12. The mouthpiece according to claim 1, wherein the light source is positioned on the lingual outer surface of the body.

13. The mouthpiece according to claim 1, wherein the body has a U- or H-shaped cross-sectional profile, which is capable of covering horizontal and two vertical surfaces of the teeth at one or both lines of teeth, respectively.

14. The mouthpiece according to claim 1, wherein the light source and the body are configured to emit an average power density of 30 to 1000 mW/cm$^2$ towards the teeth.

15. The mouthpiece according to claim 1, wherein the light source is adapted to deliver light to the tongue through the lingual outer surface of the body.

16. The mouthpiece according to claim 1, wherein the body and the light source are at least partly encapsulated by a casing having a shape of the dental arch.

17. The mouthpiece according to claim 1, further comprising at least one sensor, for measuring the response of intraoral tissue or intraoral agent to light emitted thereto, such as photobleaching of active ingredient or amount of active ingredient in the treatment area.

18. The mouthpiece according to claim 1, further comprising means for mechanically vibrating the body while positioned intraorally.

19. The mouthpiece according to claim 1, wherein the light source is adapted to emit light at least one non-visible wavelength band of 780-815 nm.

20. The mouthpiece according to claim 1, further comprising an intraoral sensor and means for regulating the output power of the light source on at least one wavelength, in particular at least one non-visible wavelength band, based on input from the intraoral sensor.

21. The mouthpiece according to claim 20, wherein said means for regulating the output power of the light source are adapted to increase power output of the light source in response to detecting a particular wavelength by said intraoral sensor.

22. The mouthpiece according to claim 1, further configured to emit simultaneously both non-visible treatment light and visible safety light, the visible safety light preferably having an intensity high enough to cause active aversion response of the eye.

23. The mouthpiece according to claim 1, wherein the light guiding material comprises a transparent polymer material, in particular a polymer material selected from the group of polyethylene terephthalate (PET), polycarbonate and acrylic polymers.

24. The mouthpiece according to claim 1, wherein said light guiding material has a refractive index equal to or greater than about 1.4.

25. The mouthpiece according to claim 1, further comprising:
   a body made of light-guiding material comprising one or more H-shape light guide elements following U-shape of dental arch, fully or partly covered with a biocompatible cover;
   a plurality of light sources are attached to the body adapted to deliver light to surface of teeth, wherein the light sources are placed between facial outer surface of the light guide and inner surface of cheek and optically coupled to H-shape light guide elements; and
   the light-source comprises LEDs, the maximum irradiance variation of the LED coupled H-shaped light guide elements at facial and lingual inner surfaces being at maximum±90% or less.

26. A method of delivering light within an intraoral photodynamic treatment mouthpiece comprising:
providing the intraoral photodynamic treatment mouthpiece comprising a body being made of light-guiding material and comprising facial and lingual outer surfaces, and facial and lingual inner surfaces adapted to face facial and lingual surfaces of teeth, respectively, in order to target light thereto through said inner surfaces, the body further comprising a reflective portion having a slanted profile and placed on the opposite side of the body than the light source for directing light towards the inner surfaces of the teeth on the opposite side of the teeth than the light source,
providing light into the body through at least one of the outer surfaces of the body, and
conducting part of said light to said facial inner surface and part of said light to said lingual surface so that at least a portion of the light travels through said body from the facial side to the lingual side, or vice versa, before exiting the body.

27. An intraoral photodynamic treatment method comprising:
providing at least one optically active agent onto surfaces of the teeth;
positioning a mouthpiece into the mouth, wherein the mouthpiece comprises a body being made of light-guiding material and comprising facial and lingual outer surfaces, and facial and lingual inner surfaces adapted to face facial and lingual surfaces of teeth, respectively, in order to target light thereto through said inner surfaces, and wherein the positioning is done such that said facial and lingual inner surfaces of the mouthpiece face the facial and lingual surfaces of the teeth, respectively, the body further comprising a reflective portion having a slanted profile and placed on the opposite side of the body than the light source for directing light towards the inner surfaces of the teeth on the opposite side of the teeth than the light source; and
delivering light within the mouthpiece and onto the facial and lingual surfaces of the teeth.

28. The mouthpiece according to claim 1, wherein the light source is located away from the line of occlusion and wherein the light source is capable of illuminating opposite surfaces of the teeth.

* * * * *